United States Patent [19]

Eissenstat et al.

[11] Patent Number: 5,330,992
[45] Date of Patent: Jul. 19, 1994

[54] 1-CYCLOPROPYL-4-PYRIDYL-QUINOLI-NONES

[75] Inventors: Michael A. Eissenstat, Town of West Sand Lake; John D. Weaver, III, Town of Northumberland; Gee-Hong Kuo, Town of East Greenbush; Mark P. Wentland, Town of Colonie, all of N.Y.

[73] Assignee: Sterling Winthrop Inc., New York, N.Y.

[21] Appl. No.: 967,473

[22] Filed: Oct. 23, 1992

[51] Int. Cl.⁵ ............... A61K 31/47; C07D 215/233
[52] U.S. Cl. ...................................... 514/312; 546/153
[58] Field of Search ........................ 546/153; 514/312

[56] References Cited

U.S. PATENT DOCUMENTS

| | | | |
|---|---|---|---|
| 4,623,650 | 11/1986 | Gilligan et al. | 514/312 |
| 4,705,788 | 11/1987 | Schriewer et al. | 514/254 |
| 4,791,118 | 12/1988 | Masuzawa et al. | 514/312 |
| 4,820,716 | 4/1989 | Petersen et al. | 514/312 |
| 4,908,366 | 3/1990 | Schriewer et al. | 514/252 |
| 4,933,335 | 6/1990 | Bridges et al. | 514/215 |
| 4,952,695 | 8/1990 | Groche et al. | 546/156 |
| 4,959,363 | 9/1990 | Wentland | 514/235.2 |
| 5,075,319 | 12/1991 | Lesher et al. | 514/312 |

Primary Examiner—Bernard Dentz
Attorney, Agent, or Firm—Richard A. Hake; Paul E. Dupont

[57] ABSTRACT

Compounds of formula

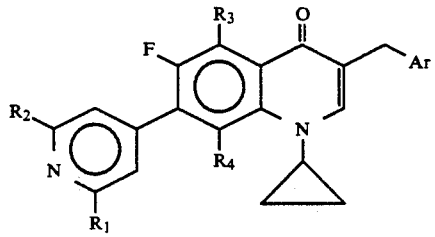

wherein
$R_1$ is hydrogen, lower-alkyl, or trifluoromethyl;
$R_2$ is lower-alkyl, trifluoromethyl or $CH_2Z$ where Z is hydroxy, chloro, lower-alkylamino or dilower-alkylamino;
$R_3$ and $R_4$ are each individually hydrogen or fluoro; and
Ar is phenyl, an aromatic 5- or 6-membered heterocycle or any of these substituted at one or more positions with lower-alkyl, fluoro, chloro, hydroxy, amino, lower-alkylamino, dilower-alkylamino, carboxy, sulfonamido, lower alkylsulfonamido, methylenedioxy, trifluoroacetamido, lower-alkanoylamino, or carbamoyl; and their pharmaceutically acceptable acid addition salts are useful as anticancer agents.

24 Claims, No Drawings

1-CYCLOPROPYL-4-PYRIDYL-QUINOLINONES

BACKGROUND OF THE INVENTION a) Field of the Invention

This invention relates to novel 1-cyclopropyl-3 substituted-5-R3-6-fluoro-8-R4-7-(2-R1-6-R2-4-pyridyl)-1,4-dihydro-quinolin-4-ones and their pharmaceutical compositions, and a method of treating malignancy with these compounds.

b) Information Disclosure Statement

Gilligan et al., U.S. Pat. No. 4,623,650 issued 18 Nov. 1986, discloses 1-substituted 6,8-difluoro-7-aryl-1,4-dihydroquinol-4-one 3-carboxylic acids stated to have antibacterial activity.

Schriewer et al., U.S. Pat. No. 4,705,788 issued 10 Nov. 1987, discloses novel antibacterially active 7-amino-1-(substituted cyclopropyl)-1,4-dihydro-4-oxo-3-quinolinecarboxylic acids of the formula

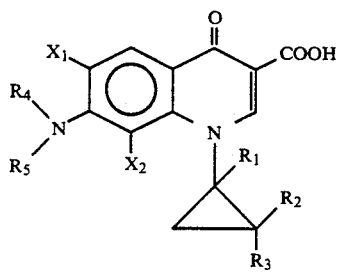

in which $X_1$ and $X_2$ can be identical or different and represent hydrogen or halogen;

$R_1$, $R_2$ and $R_3$ represent hydrogen, methyl, chlorine or fluorine, the radicals $R_1$-$R_3$ never all being identical; and $R_4$ and $R_5$, together with the nitrogen atom to which they are bonded, form a 5-membered or 6-membered heterocyclic ring which may be substituted.

Mosuzawa et al., U.S. Pat. No. 4,791,118, issued 13 Dec. 1988, discloses quinolonecarboxylic acid derivatives of the following formula

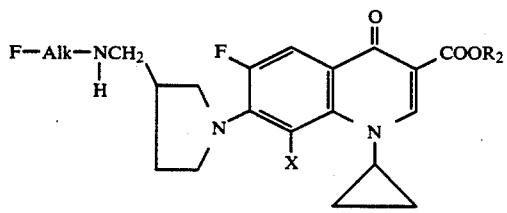

wherein

R is hydrogen atom or lower alkyl group;

Alk is lower alkylene group; and

X is hydrogen atom or halogen atom; the hydrates and pharmaceutically acceptable salts thereof are stated to be useful as antibacterial agents.

Peterson et al., U.S. Pat. No. 4,820,716, issued 11 Apr. 1989 discloses 7-(1-pyrrolidinyl)-3-quinolonecarboxylic acid derivatives of the formula

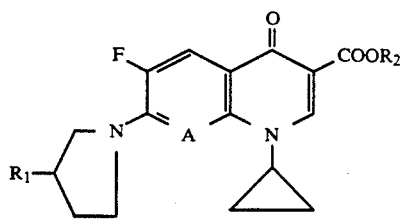

in which

A is CH, CCl, CF or N;

$R_1$ is hydroxyl, hydroxymethyl or mercapto; and $R_2$ is hydrogen, alkyl, having 1 to 4 carbon atoms or (5-methyl-2-oxo-1,3-dioxol-4-yl)methyl; with the proviso that, when R1 is hydroxy, A is not CF or N, or pharmaceutically acceptable hydrates or salts thereof are stated to be useful as antibacterials and animal feed utilization promoters.

Schriewer et al., U.S. Pat. No. 4,908,366, issued 13 Mar. 1990, discloses compounds of the formula

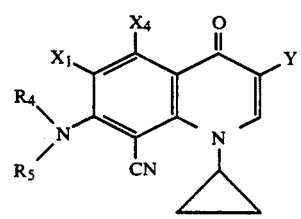

in which

Y represents a carboxyl group, a nitrile group, an ester group —$COOR_1$ or an acid amide group —$CONR_2R_3$;

$X_1$ represents hydrogen, nitro, alkyl or halogen;

$X_4$ can be hydrogen or halogen, or alkyl;

$R_4$ and $R_5$, together with the nitrogen atom to which they are bonded form a 5- or 6-membered heterocyclic ring which can additionally contain the atoms or groups —O—, —S—, —SO—, —$SO_2$—

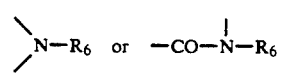

as ring members of the group

can also represent a ring system of the structure

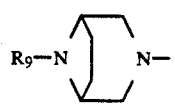

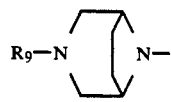

-continued

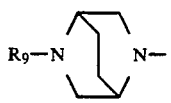

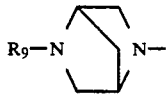

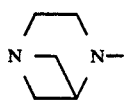

which can optionally be substituted on the ring carbons by methyl and pharmaceutically usable hydrates, salts or esters thereof.

These compounds are stated to have a high antibacterial activity and therefore to be suitable as active compounds for human and veterinary medicine.

Bridges et al., U.S. Pat. No. 4,933,335, issued 12 Jun. 1990, discloses a series of quinolone carboxylic acids which are stated to have use as antibacterial agents.

Groche et al., U.S. Pat. No. 4,952,695, issued 28 Aug. 1990, discloses 1-cyclopropyl-6,7,8-trifluoro-1,4-dihydro-4-oxoquinoline-3-carboxylic acid and ester as pharmaceutical intermediate.

Wentland, U.S. Pat. No. 4,959,363, issued 25 Sep. 1990, discloses compounds of the formula

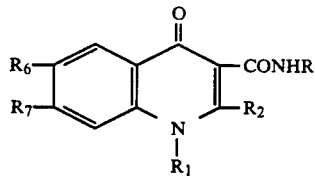

where

R is hydrogen, hydroxy, amino or lower-alkyl;

$R_1$ is lower-alkyl, lower-alkenyl, cycloalkyl, pyridinyl, phenyl or substituted phenyl $R_2$ is hydrogen, amino or hydroxy;

$R_6$ is hydrogen or fluoro; and $R_7$ is phenyl, pyridinyl or selected other heterocycles;

The compounds are stated to have antiviral activity against herpes virus.

Lesher et al., U.S. Pat. No. 5,075,319, dated Dec. 24, 1991, discloses fluorinated 1-cyclopropyl-7-(substituted-pyridinyl)-1,4-dihydro-4-oxo-3-quinolinecarboxylic acids of the formula

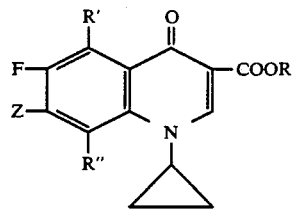

wherein

R is hydrogen;

R' and R" are hydrogen or fluoro, or other groups; and

Z is 3- or 4-pyridinyl substituted by alkyl groups or substituted alkyl groups. The compounds are stated to be superior antibacterial agents.

SUMMARY OF THE INVENTION

The invention resides in one aspect in novel 1-cyclopropyl-3-ArCH$_2$-5-R$_3$-6-fluoro-8-R$_4$-7-(2-R$_1$-6-R$_2$-4-pyridyl)-1,4-dihydroquinolin-4-ones useful as antineoplastic agents.

In another aspect, the invention relates to novel 1-cyclopropyl-3-ArCH$_2$-5-R$_3$-6-fluoro-8-R$_4$-7-(2-R$_1$-6-R$_2$-4-pyridyl)-1,4-dihydroquinolin-4-ones in which Ar contains one or more lower-alkoxy or benzyloxy substituents. These compounds are useful as intermediates in the preparation of the corresponding hydroxy compounds.

The invention further relates to 1-cyclopropyl-5-R$_3$-6-fluoro-8-R$_4$-7-(2-R$_1$-6-R$_2$-4-pyridyl)-1,2,3,4-tetrahydroquinoline-4-ones which are useful as intermediates for preparing the 1-cyclopropyl-3-ArCH$_2$-5-R$_3$- 6-fluoro-8-R$_4$-7- ( 2-R$_1$-6-R$_2$-4 pyridyl) -1,4-dihydroquinoline-4 -ones.

In another aspect the invention relates to pharmaceutical compositions containing as an active ingredient 1-cyclopropyl-3-ArCH$_2$-5-R$_3$-6-fluoro-8-R$_4$-7-(2-R$_1$-6-R$_2$-4-pyridyl)-1,4-dihydroquinolin-4-ones and their pharmaceutically acceptable salts.

In yet another aspect, the invention relates to a method of inhibiting the growth of or killing malignant cells in a mammal afflicted with malignant cells, which comprises administering to said mammal an effective amount of a compound of the invention or a pharmaceutically acceptable salt thereof or composition of the invention in an effective amount to inhibit the growth or induce the regression of these cells.

DETAILED DESCRIPTION INCLUSIVE OF PREFERRED EMBODIMENTS

Specifically, the present invention relates to compounds of formula I

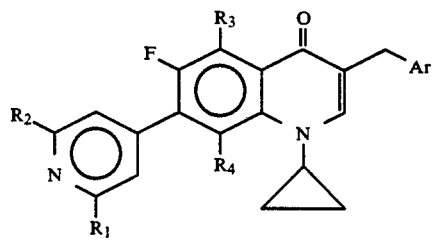

wherein $R_1$ is hydrogen, lower-alkyl, or trifluoromethyl;

$R_2$ is lower-alkyl, trifluoromethyl or $CH_2Z$ where Z is hydroxy, chloro, lower-alkylamino or dilower-alkylamino $R_3$ and $R_4$ are each independently hydrogen or fluoro; and Ar is phenyl, an aromatic 5- or 6-membered heterocycle or any of these substituted at one or more positions with lower-alkyl, fluoro, chloro, hydroxy, amino, lower-alkylamino, dilower-alkylamino, carboxy, sulfonamido, lower-alkylsulfonamido, methylenedioxy, trifluoroacetamido, lower-alkanoylamino, or carbamoyl; or pharmaceutically acceptable acid addition salts thereof and to pharmaceutical compositions and methods of use thereof in the treatment of malignancy.

Preferred compounds of formula I are those wherein $R_1$ and $R_2$ are methyl, $R_3$ is hydrogen and $R_4$ is fluoro.

The invention also relates to compounds of formula Ia

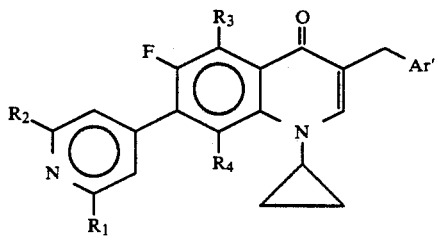

wherein $R_1$ is hydrogen, lower-alkyl, or trifluoromethyl;

$R_2$ is lower-alkyl, trifluoromethyl or $CH_2Z$ where Z is hydroxy, chloro, lower-alkylamino or dilower-alkylamino $R_3$ and $R_4$ are each independently hydrogen or fluoro; and Ar' is phenyl or an aromatic 5- or 6-membered heterocycle substituted with one or more lower-alkoxy or benzyloxy substituents. These compounds are useful as intermediates in the preparation of compounds of formula I wherein Ar is phenyl or an aromatic 5- or 6-membered heterocycle substituted with one or more hydroxy groups.

The invention further relates to tetrahydroquinolines having formula III

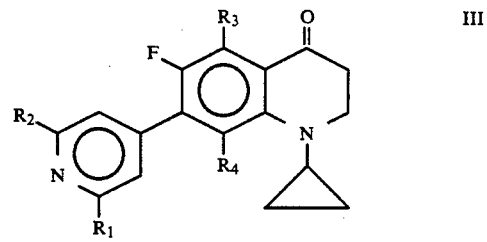

wherein $R_1$, $R_2$, $R_3$ and $R_4$ have the previously given meanings. These compounds are useful as intermediates for preparing the compounds of formulas I and Ia.

Aromatic 5- or 6-membered heterocycle refers to unsaturated heterocyclic rings containing nitrogen and/or oxygen such as pyridyl, furanyl, isoxazolyl, pyrrolyl, oxazolyl, pyrimidyl, imidazolyl and the like. Lower-alkyl refers to a hydrocarbon radical of 1 to about 4 carbon atoms including, methyl, ethyl, propyl, isopropyl, butyl, secbutyl and the like. Lower-alkoxy refers to alkoxy with 1 to about 4 carbon atoms, such as methoxy, ethoxy, propoxy, isopropoxy, butoxy, secbutoxy and the like. Lower-alkanoyl refers to an alkanoyl group having about 2 to 4 carbon atoms and thus includes acetyl, propionyl, isobutyryl and the like.

The compounds of formula I may be prepared according to the following scheme:

Scheme I

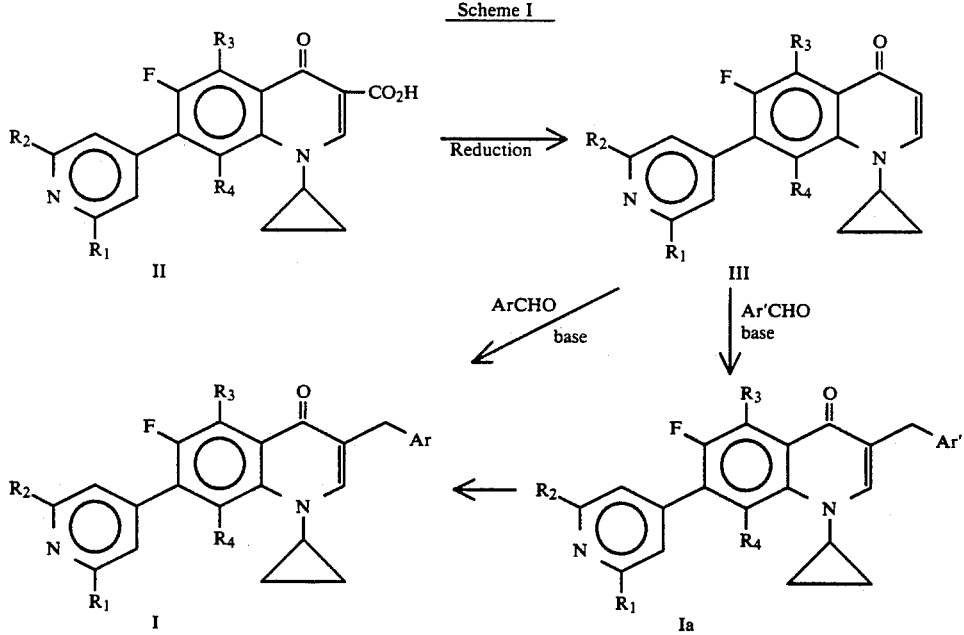

The preparation of starting materials of formula II is described in U.S. Pat. No. 5,075,319, which is incorporated herein by reference. Acid II is then reduced, for example with a complex metal hydride, for example sodium borohydride or the like, to afford quinolone III, which is then condensed with an aldehyde (ArCHO) in the presence of base, by methods well known in the art to give compounds of formula I. In cases where Ar is to be substituted with hydroxy, it is preferred that the aldehyde when condensed have the hydroxyl protected as an ether (Ar'CHO). Then, in a later step, the ether is cleaved by methods well known in the art, for example by reaction with HBr or BBr$_3$.

The aldehydes used as starting materials are either commercially available, known or may be prepared by procedures known in the art.

Simple chemical transformations which are conventional and well known to those skilled in the art of chemistry can be used for effecting changes in functional groups in the compounds of the invention. For example, acylation of hydroxy- or amino-substituted species to prepare the corresponding esters or amides, respectively; cleavage of methyl or benzyl ethers to produce the corresponding alcohols or phenols; and hydrolysis of esters or amides to produce the corresponding acids, alcohols or amines as desired can be carried out.

The compounds of the invention are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anion. In practicing the present invention, it is convenient to form the hydrochloride, fumarate, toluenesulfonate, hydrogen sulfate, methanesulfonate or maleate salts and the like. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification of identification, or when it is used as an intermediate in preparing a medicinally acceptable salt by ion exchange procedures.

The structures of the compounds of the invention were established by the mode of synthesis, by elemental analysis, and by infrared, nuclear magnetic resonance, and mass spectroscopy. The course of the reactions and the identity and homogeneity of the products were assessed by thin layer chromatography (TLC) and high-pressure liquid chromatography (HPLC) and melting point.

The following examples illustrate the invention, but however do not limit it thereto.

Preparation of Intermediates

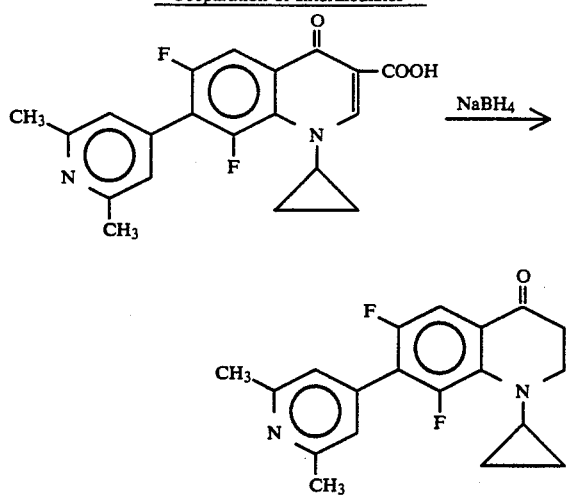

Preparation 1: 1-Cyclopropyl-6, 8-difluoro-1,2,3,4-tetrahydro-7-(2,6-dimethyl-4-pyridinyl) -3-quinolin-4-one Sodium borohydride (10.0 g was added in portions over 35 min to a slurry of 20.0 g (0.054 mol) 1-cyclopropyl-7-(2,6-dimethyl-4-pyridinyl) -6, 8-difluoro-1,4-dihydro-4-oxo-3-quinolinecarboxylic acid (Formula II $R_1=R_2=CH_3$, $R_3$=hydrogen,$R_4$=F), described in U.S. Pat. No. 5,075,319, in 1L methanol. During this addition a vigorous gas evolution was noted. The resulting yellow solution was concentrated and the residue stirred in water (500 mL for 14 hours at 25° C. The solid that separated was collected and recrystallized from ethyl acetate to give 6.7 g (38%) of product, mp 130°-131° C. The mother liquors from the recrystallization were concentrated and dissolved in ethyl acetate. Upon cooling, an additional 9.8 g (93% combined yield) of a compound of formula III ($R_1=R_2=CH_3$, $R_3$=hydrogen,$R_4$=F) was obtained.

Aldehydes used for the preparation of compounds of formula I from The product of preparation 1 are commercially available, known or prepared by known methods.

Preparation 2: 2-Benzyloxy-3-fluorobenzaldehyde

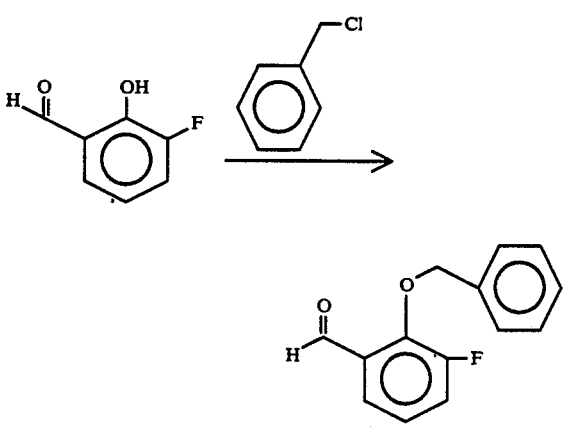

0.49 mL (4.3 mmol) Benzyl chloride was added to a mixture of 0.98 g (7.1 mmol) K$_2$CO$_3$, 5 mL acetonitrile and 0.5 g (3.6 mmol) of 3-fluoro salicaldehyde. The mixture was heated to 50° C. for 24 hrs. Upon cooling the mixture was extracted with water then thrice with ethyl acetate. The ethyl acetate extracts were combined, dried over MgSO₄ and concentrated in vacuo to a yellow oil, yielding 760 mg (92%) 2-benzyloxy 3-fluoro, benzaldehyde, which was used in the preparation of Example 20 without further purification.

Compounds of formula I were prepared by two methods as described below in examples 1 and 2 (methods A and B, respectively).

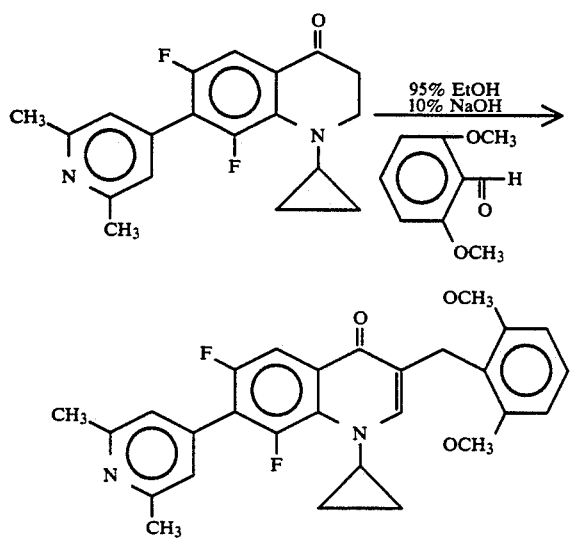

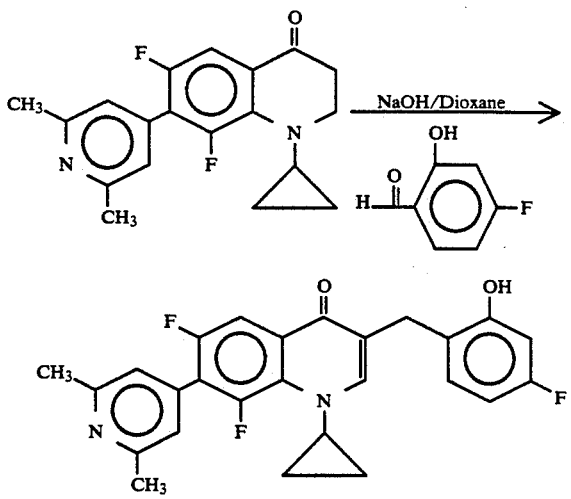

Example 1: Preparation of 1-Cyclopropyl-6,8-difluoro-7-[2,6-dimethyl-4-pyridinyl]-3-[2,6-dimethoxyphenylmethyl]-1,4-dihydroquinolin-4-one (Method A)

400 mg (1.2 mmol) of the product of preparation 1 was dissolved in 5 mL of 95% ethanol and 5 mL of 10% sodium hydroxide. Then, 398 mg (2.9 mmol) of 2,6-dimethoxybenzaldehyde was added and the resulting orange suspension was stirred at room temperature for 45 minutes. Five drops of 35% sodium hydroxide was added and the mixture warmed to 60° C. for 2 hrs. After cooling the reaction mixture was quenched with saturated ammonium chloride and extracted thrice with ethyl acetate. The ethyl acetate layers were combined and dried over MgSO₄. Filtration and concentration in vacuo provided an off-white solid. Recrystallization from ethyl acetate afforded a compound of formula I ($R_1 = R_2 = CH_3$, $R_3$ = hydrogen, $R_4$ = F, Ar = 2,6-dimethoxyphenyl), as a white solid 416 mg (73%), m.p. 191-192° C.

Example 2: Preparation of 1-cyclopropyl-6,8-difluoro-7-[2,6-dimethyl-4-pyridinyl]-3-[4-fluoro-2-hydroxyphenylmethyl]-4(H)-quinolone (Method B)

200 mg (0.60 retool) of the product of preparation 1, (formula III $R_1 = R_2 = CH_3$, $R_3$ = hydrogen, $R_4$ = F) 87 mg (0.62 mol) 4-fluoro-2-hydroxybenzaldehyde and 325 mg (8.1 mmol) sodium hydroxide in 10 mL of dioxane were heated at reflux for 1 hr. The reaction mixture was concentrated in vacuo and the resulting residue was dissolved in toluene. The toluene layer was placed on a silica column and eluted with 40% ethyl acetate/hexane. The most polar component was concentrated in vacuo and recrystallized from CHCl₃/ether to provide 39.4 mg (13%) of a compound of formula I, ($R_1 = R_2 = CH_3$, $R_3$ = hydrogen, $R_4$ = F Ar = 4-fluoro-2-hydroxyphenyl), mp 244°-245° C.

Following procedures substantially as described in Examples 1 and 2 (methods A and B respectively), reaction of the product of preparation 1 with an appropriate aidehyde, ArCHO, afforded the following compounds (examples 3-25) of formula I, wherein $R_1$ and $R_2$ are methyl, $R_3$ is hydrogen, and $R_4$ is fluoro. Certain notations are shortened for use in Tables: hexane refers to mixed hexanes, nBuOH is n-Butanol, i-PrOH is isopropanol, EtOAc is ethyl acetate, TBME is t-butyl methyl ether, EtOH is ethanol,

TABLE 1

Synthesis of Compounds of Formula I

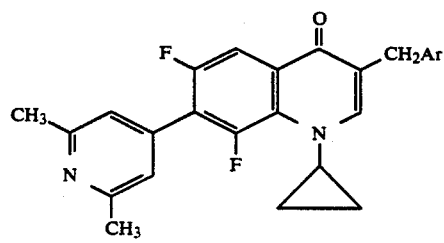

| Example | Ar = | Method | Yield (%) | Rec. solv. | m.p. (°C.) |
|---|---|---|---|---|---|
| 3 | Phenyl | A | 45 | EtOAc/Hexane | 190-192 |
| 4 | 2-pyridyl | A | 30 | EtOAc/Hexane | 190-192 |

TABLE 1-continued

Synthesis of Compounds of Formula 1

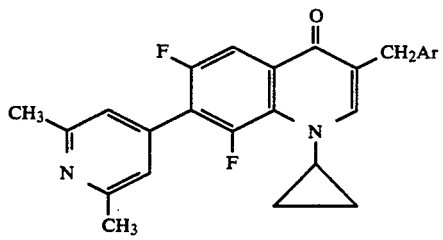

| Example | Ar = | Method | Yield (%) | Rec. solv. | m.p. (°C.) |
|---|---|---|---|---|---|
| 5 | 3,4,5-(CH$_3$O)$_3$-Phenyl | A | 32 | EtOAc/Hexane | 170–171 |
| 6 | 4-Cl-Phenyl | A | 49 | Ether | 203–204 |
| 7 | 4-CH$_3$O-Phenyl | A | 52 | EtOAc/Hexane | 167–168 |
| 8 | 2-(CH$_3$O)-Phenyl | A | 55 | EtOAc/Ether | 149–150 |
| 9 | 3-(CH$_3$O)-Phenyl | A | 45 | EtOAc/Ether | 147–148 |
| 10 | 3,4-(OCH$_2$O)-Phenyl | A | 54 | i-PrOH | 181–182 |
| 11 | 2,3-(CH$_3$O)$_2$-Phenyl | A | 47 | EtOAc/Ether | 133–135 |
| 12 | 2,4-(CH$_3$O)$_2$-Phenyl | A | 64 | EtOAc/Hexane | 180–181 |
| 13 | 4-pyridyl | A | 31 | TBME | 155–157 |
| 14 | 2,4,6(CH$_3$O)$_3$-Phenyl | A | 56 | Ether/Hexane | 175–176 |
| 15 | 2(HOOC)-Phenyl | A | 47 | CH$_2$Cl$_2$/Ether | >300 |
| 16 | 2-pyrrolyl | A | 46 | CH$_2$Cl$_2$/Hexane | 229–231 (decom) |
| 17 | 2,4(CH$_3$O)$_2$3-CH$_3$-Phenyl | A | 63 | Ether/Hexane | 138–140 |
| 18 | 2-imidazolyl | A | 40 | CH$_3$CN/Ether | 220–223 (decom) |
| 19 | 4-CH$_3$CONH-Phenyl | B | 48 | CH$_2$Cl$_2$ | 265–268.5 |
| 20 | 2-C$_6$H$_5$CH$_2$O-3-F-Phenyl | A | 87 | Ether/Hexane | 68–69 |
| 21 | (2-CH$_3$-3-OH-5-HOCH$_2$-4-pyridyl) | A | 62 | EtOAc/Hexane | 156–158 |
| 22 | 2-(CF$_3$CONH)-Phenyl | B | 70 | EtOAc/Hexane | 246.5–247.5 |
| 23 | 2,5(CH$_3$O)$_2$-Phenyl | A | 65 | EtOAc/Hexane | 168–170 |
| 24 | 4-imidazolyl | A | 20 | CH$_3$CN/Ether | 208–211 |
| 25 | 2-(CH$_3$SO$_2$NH)-Phenyl | B | 6 | Ether/Hexane | 217.0–218.5 |

Several of the examples prepared by the methods above with ether substituents can be treated to cleave the ether linkages, yielding hydroxy compounds. The following examples illustrate the two common methods employed to prepare compounds of formula 1 with hydroxy substituents on the aromatic group from their alkyloxy precursors.

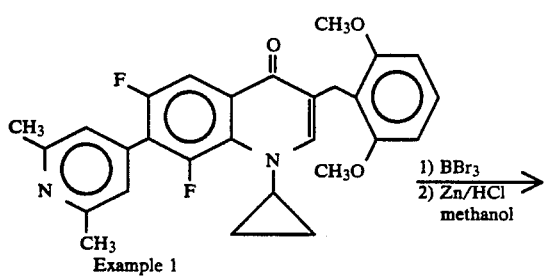
Example 1

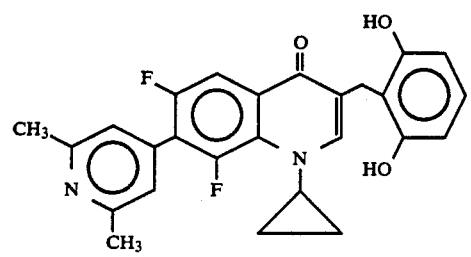

Example 26: Preparation of:
1-Cyclopropyl-6,8-difluoro-7-[2,6-dimethyl-4-pyridinyl]-3-[2,6-dihydroxyphenylmethyl]-1,4-dihydroquinoline-4-one (Method C)

299 mg (0.63 mmol) of the compound of example 1 was dissolved in 15 mL of CH$_2$Cl$_2$ and cooled to 0° C. 1.8 mL of boron tribromide were added over 45 minutes and the resulting suspension was stirred and warmed to room temperature for 2 hrs. The reaction mixture was concentrated in vacuo and then chilled on ice. 15 mL of cold 2N HCl and 2 mL of cold methanol were added. The resulting solution was heated at 100° C. for 3 hrs. After cooling the solution was adjusted to pH=5–6 with 35% NaOH and then brought to pH=7–8 with saturated NaHCO$_3$. The solids which precipitate were filtered and saved. The aqueous NaHCO$_3$ solution was extracted 3X with 10% butanol/CHCl$_3$. The organic layers were combined with the solid precipitate and the resulting solution was dried over MgSO$_4$. Filtration and concentration in vacuo provides a yellow solid. Recrystallization from CHCl$_3$/hexane provides 147 mg (52%) of a compound of formula I, (R$_1$=R$_2$=CH$_3$, R$_3$=hydrogen, R$_4$=F, Ar=2,6-dihydroxy phenyl), melting point 308°–310° C.

hydroxyarylmethyl compounds of Table 2 (examples 28–38).

TABLE 2

Synthesis of compounds of Formula I

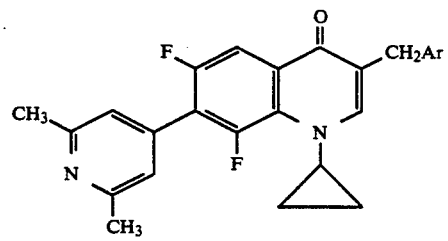

| Example | Ar = | Starting Material Ex No. | Method | Yield (%) | Recrystal solvent | m.p. (°C.) |
|---|---|---|---|---|---|---|
| 28 | 3,5-(OCH$_3$)$_2$4-OH-phenyl | 3 | D | 28 | Acetone/CHCl$_3$ | 210–212 |
| 29 | 3,4,5-(OH)$_3$-phenyl | 3 | D | 43 | CHCl$_3$ | 270–272 |
| 30 | 2-OH-phenyl | 6 | D | 66 | CHCl$_3$/Ether | 141–142 |
| 31 | 3-OH-phenyl | 7 | D | 73 | CHCl$_3$/Ether | 144–145 |
| 32 | 3,4-(OH)$_2$-phenyl | 8 | C | 30 | EtOAc | 266–268 |
| 33 | 2,4-(OH)$_2$-phenyl | 10 | C | 87 | EtOAc | 276–278 |
| 34 | 2,3-(OH)$_2$-phenyl | 9 | C | 87 | EtOAc | 242–244 |
| 35 | 2,4,6-(OH)$_3$-phenyl | 13 | C | 90 | i-PrOH/Ether | 245–247 |
| 36 | 2,4-(OH)$_2$-3-CH$_3$-phenyl | 16 | C | 61 | n-BuOH/CHCl$_3$ | 268–270 |
| 37 | 2-OH-3-F-phenyl | 17 | C | 70 | CHCl$_3$/Ether | 227–229 |
| 38 | 2,5-(OH)$_2$-phenyl | 22 | C | 72 | n-BuOH/Ether | 256–258 |

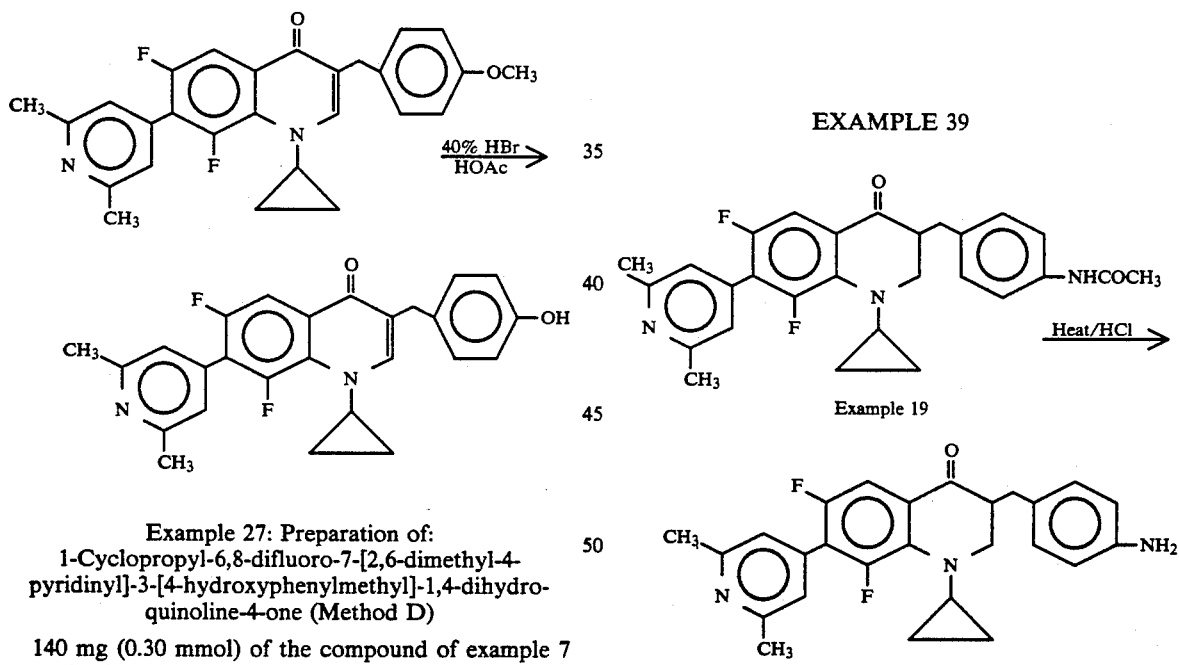

EXAMPLE 39

Example 27: Preparation of: 1-Cyclopropyl-6,8-difluoro-7-[2,6-dimethyl-4-pyridinyl]-3-[4-hydroxyphenylmethyl]-1,4-dihydroquinoline-4-one (Method D)

140 mg (0.30 mmol) of the compound of example 7 was dissolved in 1 mL 40% HBr and 1 mL acetic acid under nitrogen and heated to reflux for 3 hrs. Upon cooling, the reaction was basified with cold saturated potassium carbonate to pH=8. The aqueous layer was extracted with ethyl acetate (3X 20 mL). The ethyl acetate layer was dried over MgSO$_4$, filtered and concentrated in vacuo to afford a tan solid. Recrystallization from CHCl$_3$/ ether gave 103 mg (76%) of a compound of formula 1 [R$_1$=R$_2$=CH$_3$, R$_3$=hydrogen, R$_4$=F, Ar=4-HO phenyl], m.p. 258°–259° C.

Following procedures substantially as described in examples 26 and 27 (hereinafter Methods C and D respectively), alkoxy- or benzyloxy-arylmethyl compounds of Table 1 were converted to the corresponding 101 mg of Example 19 and 2 mL 1N HCl were heated at reflux for 2 hours. Upon cooling the reaction mixture was basified with saturated sodium bicarbonate and extracted five times with ethyl acetate, dried over MgSO$_4$ and concentrated to a solid in vacuo. The solid was taken up in ethyl acetate and put through a silica gel column, eluted with 80% ethyl acetate/20% hexane. The eluent was concentrated in vacuo and triturated with ether to give white crystals. Hexane was added to give additional crystals of the same material, yielding 72.5 m9 (79%) of a compound of formula I (R$_1$=R$_2$=CH$_3$, R$_3$=hydrogen, R$_4$=F, Ar=4-NH$_2$ phenyl), m.p. 216.5°–219.5° C.

EXAMPLE 40

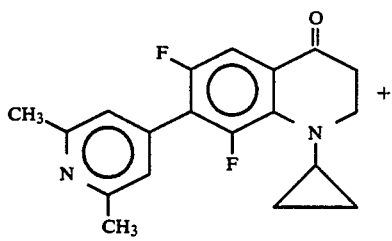

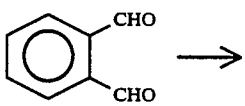

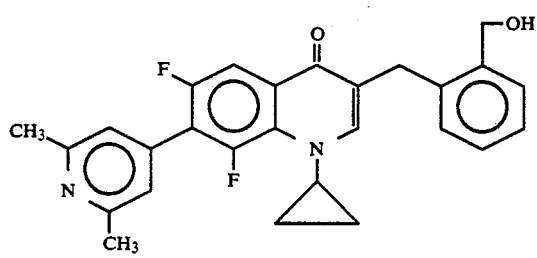

2.68 g (20 mmol) 1,2-Benzenedicarboxaldehyde was dissolved in 15 mL 95% ethanol. The mixture was heated to 40° C. and added to 328 mg (1 retool) of the product of preparation 1 dissolved in 12 mL 10% sodium hydroxide and 12 mL 95% ethanol. After 4 hours, 2 mL 35% NaOH was added and the mixture was stirred at 40° C. for 15 hours. Upon cooling saturated ammonium chloride was added to the reaction mixture and it was extracted with ethyl acetate thrice. The organic fractions were combined and passed through a 20 cm silica gel column and which was then eluted with ethyl acetate/hexane gradient (1:1 to7:1). The product eluted as a yellow-brown oil, which was concentrated in vacuo and then recrystallized from acetonitrile and ether to give lightly colored yellow crystals, 42 mg (9%) of a compound of formula I ($R_1=R_2=CH_3$, $R_3$=hydrogen, $R_4=F$, Ar=2-($CH_2OH$)-phenyl), m.p. 185°–187° C.

EXAMPLE 41

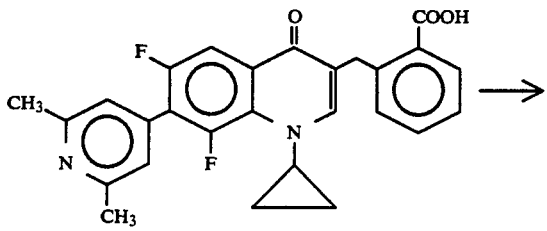

Example 17

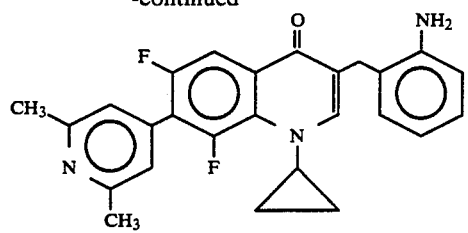

Example 41a a) 276 mg (0.6 mol) Example 17 was added to 1.277 g (0.66 mmol) diphenyl phosphoryl azide; 1.45 g (14.3 mmol) triethylamine, 2 mL tert-butanol and was stirred at 110° C. (reflux) for 15 hours. Upon cooling approximately 6 mL 6N HCl and 2 mL methanol was added. The mixture was then heated at reflux for 4 hours and then basified with 10% NaOH to pH 8. The reaction mixture was then extracted with methylene chloride thrice. The organic fractions were dried over sodium sulfate and concentrated in vacuo. The residue was then taken up in methylene chloride and passed through an 18-cm silica gel column. The column was eluted with a gradient of methylene chloride and acetone from 1/0 to 3/1 (volume/volume), the product concentrated in vacuo, and recrystallized from acetonitrile, yielding 80 mg (31%) of an off-white solid of formula I ($R_1=R_2=CH_3$, $R_3$=hydrogen, $R_4=F$, Ar=2-($NH_2$) phenyl), m.p. 225°–227° C.

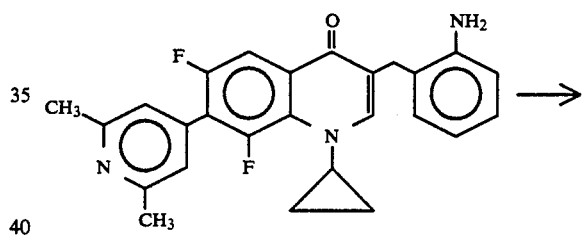

Example 41a

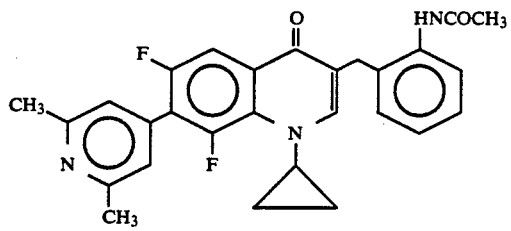

Example 41b 30 mg of Example 41a and 0.75 mL acetic anhydride was dissolved in 0.6 mL pyridine and 4 mL methylene chloride at 0° C. The mixture was stirred at for 20 hours, and the solvent was then removed in vacuo. The residue was put on a 20 cm silica gel column and eluted with an ethyl acetate/hexane gradient from 1/1 to 7/1 to give product which was recrystallized from methylene chloride/hexane to give 31 mg (94%) of an off-white solid of formula I $R_1=R_2=CH_3$, $R_3$=hydrogen, $R_4=F$, Ar=2-($NHCOCH_3$)-phenyl], m.p. 222°–224° C.
By reacting any of the following aldehydes:
oxazole-2-carboxaldehyde,
2,4-dimethyloxazole-5-carboxaldehyde,
pyrimidine-2-carboxaldehyde,
4-(N,N-dimethylamino)benzaldehyde,
2-furaldehyde, 3-furaldehyde,
isoxazolyl-3-carboxaldehyde and
isoxazole-5-carboxaldehyde
with the product of preparation 1, in a manner substantially as described in method B, it is contemplated that the corresponding compounds of formula I can be prepared in which Ar is 2-oxazolyl, 2,4-dimethyl-5-oxazolyl, 2-pyrimidinyl, 4 (N, N-dimethylamino) phenyl, 2-furanyl, 3-furanyl, 3-isoxazolyl and 5-isoxazolyl, respectively.

It is contemplated that the following intermediates of formula II (described in U.S. Pat. No. 5,075,319, which is incorporated herein by reference) 1-cyclopropyl-6-fluoro-1,4-dihydro-7- (2, 6-di(trifluoromethyl)-4-pyridinyl) -4-oxo-3-quinoline carboxylic acid, 1-cyclopropyl-6,8-difluoro-1,4-dihydro-7- (2-ethyl,6-hydroxymethyl)-4-pyridinyl)-4-oxo-3-quinoline carboxylic acid, 1-cyclopropyl-5,6,8-trifluoro-1,4-dihydro-7-(2-methyl, 6-methoxymethyl-4-pyridinyl)-4-oxo-3-quinolinone carboxylic acid, 1-cyclopropyl-6-fluoro-1,4-dihydro-7-(2-ethyl,6-chloromethyl)-4-pyridinyl)-4-oxo-3-quinoline carboxylic acid, 1-cyclopropyl-6-fluoro-1,4-dihydro-7-(2-isopropyl,6-methylaminomethyl-4-pyridinyl)-4-oxo-3-quinoline carboxylic acid, when reduced with sodium borohydride as described in preparation 1 above, yield corresponding intermediates of formula III.

It is further contemplated that the intermediates of formula III, when condensed with any of the aldehydes described above according to Method A or B, yield the corresponding compounds of formula I.

Biological Properties

Topoisomerase II has been identified as the cellular target for a number of therapeutically important antineoplastic classes of drugs (Glisson and Ross, Pharmacol. Ther. 32, 89–106, 1987; Liu, Ann. Rev. Biochem. 58, 351–375, 1989). These chemically distinct agents include intercalating anthracyclines, aminoacridines, and ellipticines as well as the non-DNA intercalating epipodophyllotoxins. The intracellular effects of these agents (Zwelling et al., Biochem. 20, 6553–6563, 1981; Long et al., Blochem. 23, 1183–1188, 1984; Rowe et al. Biochem. Pharmacol. 34, 2483–2487, 1985; Rowe et al., Cancer Res. 46, 2021–2026, 1986; Kerrigan et al., NCI Monographs 4:117–121, 1987; Covey et al., Cancer Res. 48, 860–865, 1988), in addition to their topoisomerase II reactivity in vitro (Nelson et al., Proc. Natl. Acazd. Sci. 81, 1361–1365, 1984; Tewey et al., J. Biol. Chem. 259, 9182–9187, 1984a; Tewey et al., Science 266, 466–468, 1984b; Ross et al., Cancer Res. 44, 5857–5860, 1984; Chen et al., J. Biol. Chem. 259, 13560–13566, 1984; Rowe et al., Cancer Res. 46, 2021–2026, 1986), implicate topoisomerase II inhibition as central to the cytotoxicity and antitumor activity of these antineoplastic agents. Additionally the mechanisms of resistance observed in several antineoplastic agent resistant cell lines appears to be a consequence of either an alteration in the topoisomerase enzyme molecule (Pommier et al., Cancer Res. 46, 3075–308a, 1986; Glisson et al., Cancer Res. 46, 1934–1938, 1986; Esty et al., Biochem. Biophys. Res. Commun. 144, 787–793, 1987; Danks et al., Biochem. 27, 8861–8869, 1988; Sinha et al., Cancer Res. 48, 5096–5100, 1988) or its level (Per et al., Mol. Pharmacol. 32, 17–25, 1987). This evidence has clearly established topoisomerase II inhibition as a means of deriving an antitumor effect.

The compounds of the invention are inhibitors of mammalian topoisomerase II thus indicating their use as cytotoxic and antieoplastic agents in the chemotherapy of cancer in mammals.

Mammalian Topoisomerase II Inhibition Assay Procedure

The inhibition of human topoisomerase II (hereafter topo II) was quantitated by a procedure adapted from that described by Trask et al., EMBO J., 3, 671–676 (1984). The assay quantitates the amount of topo II covalently complexed by DNA at equilibrium during a topo II reaction. This assay determines the potential of a compound to stabilize this complex, which potential is closely related to the cytotoxicity of the compound.

Topo II was purified from late log phase suspension cultures of HeLa WIS by an adaptation of the method described by Per et al., Mol. Pharmacol., 32, 17–25 (1987).

Assays (in duplicate) were assembled at 4° C. Assay mix (25 $\mu$l) was distributed in Beckman (No. 265270) 1.5 mL microtitre tubes followed by the addition of 5 $\mu$l test to yield the final concentrations of assay components:

50 mM Tris-Cl pH 7.9
44 mM NaCl
10 mM MgCl2
0.6 mM DTT
0.5 mM EDTA
30 $\mu$g/ml BSA
0.5 mM ATP
5.5% (w/v) glycerol
4 ng 3' end labeled ($^{32}$P) pBR322 DNA ($10^7$ DMP/$\mu$g)
10 units Topo II The assay mix including the test compound was incubated for 20 minutes at 37° C. The reaction was terminated at 37° C. by the addition of 3 $\mu$l 10% SDS followed by the addition of 266 $\mu$l 10 mM Tris-Cl pH 7.5, 20 $\mu$g/ml BSA, 20 $\mu$g/ml calf thymus DNA, 1% SDS.

A SDS/protein precipitate was formed by the addition of 28 $\mu$l 2.5M KCl followed by chilling on ice for a minimum of 10 minutes. The precipitate was collected and washed with a Brandell cell harvester on a GFB glass fiber filter membrane as follows. The contents of the assay tube were drawn up into the harvester. The tube was then rinsed 7X with 10 mM Tris-Cl pH 7.5, 1 mM EDTA and 100 mM KCl. The precipitate was washed with 1 L of a solution of 10 mM Tris-Cl pH 7.5, 1 mM EDTA, 100 mM KCl followed by 1 L of 95% ethyl alcohol and finally 0.5 L 70% of ethyl alcohol (per 48 samples in each case). After drying, CPM was determined by liquid scintillation counting with 5 ml Biofluor (NEN Research Products) or Readisafe (Beckman Instruments Inc.) cocktail.

Preparation of test compound—A stock solution (6 mg/ml) of test compound was prepared either in 0.1N sodium hydroxide or 0.2 N hydrogen chloride. This solution then was diluted 1/5 into water and serially thereafter in either 0.02N sodium hydroxide or 0.04N hydrogen chloride, respectively. The stock solution and serial dilution of the test compound was stored at −20° C. prior to testing.

Screening of test compound—As an initial screen, the test compound was tested at a final concentration of 2, 20 and 200 $\mu$g/ml. The compound was then retested at a range of concentrations (usually 2-3X steps) bridging their approximate $EC_{50}$'s, as estimated by the prescreen.

Controls—A solvent control which indicates the base level of topo II-DNA complex formed in the absence of the test compound was included in each test. A control, in which topo II was omitted, was included for each test compound at the highest drug concentration tested.

Reference Agent—A dose response curve with mAMSA at 0.01, 0.08, 0.16, 0.32, 1.0 and 10 μg/ml was included in each test.

Data reduction—The $EC_{50}$ (effective concentration at which 50% of the maximal DNA-topo II complex is formed) of a test compound is defined to be the concentration with activity equal to the $EC_{50}$ of the reference agent, mAMSA. The maximal DNA-topo II complex formed is taken as that equal to that formed at the nearly saturating dose of mAMSA (10 μg/ml).

The results obtained for representative compounds of the invention in the human topoisomerase II assay procedure expressed as $EC_{50}$s (μM) are presented in Table 3 below.

TABLE 3

Topoisomerase Inhibition Activity

| Example | TopoII Inh. $EC_{50}$ (uM) |
|---|---|
| 1 | 37 |
| 2 | 1.0 |
| 3 | 3.9 |
| 4 | 12 |
| 5 | >190 |
| 6 | 7.7 |
| 7 | 14*E |
| 8 | 11 |
| 9 | 14 |
| 10 | 34* |
| 11 | >210 |
| 12 | >210 |
| 13 | 9.1 |
| 14 | >190 |
| 15 | 200 |
| 16 | 5.1 |
| 17 | >210 |
| 18 | 1.1 |
| 19 | 47 |
| 20 | >90 |
| 21 | 4.6 |
| 22 | 4.7 |
| 23 | 20 |
| 24 | 1.6 |
| 25 | 3.3 |
| 26 | 0.096 |
| 27 | 1.2 |
| 28 | 7.6 |
| 29 | 0.60 |
| 30 | 0.33 |
| 31 | 1.1 |
| 31 | 0.63 |
| 32 | 0.16 |
| 34 | 0.36 |
| 35 | 0.098 |
| 36 | 0.20 |
| 37 | 0.15 |
| 38 | 0.16 |
| 39 | 7.2 |
| 40 | 6.8 |
| 41a | 2.1 |
| 41b | 5.1 |

*Bell-shaped curve, E = extrapolated.

Malignant Cell Cytotoxicity Assays

Examples of compound I having Topo II activity were tested for malignant cell cytotoxicity. In vitro cytotoxicity was assayed by determining cell survival following exposure of P388 murine leukemia cells to a range of test compound concentrations. Cytotoxicity was quantitated following either a one-hour exposure or continuous exposure of P388 cells to test compound.

Cytotoxicity following a one-hour exposure of cells to drug was assayed by quantitating clonogenic cell survival according to a published procedure [Freshney, R. L. (1987) Culture of Animal Cells. A Manual of Basic Technique. Wiley-Liss Inc., New York, N.Y., pp. 140–144]. Briefly, following drug exposure cells were plated in soft agar and incubated (37°, 5% $CO_2$) for 7–10 days during which time viable cells form visible colonies. Cytotoxicity following continuous exposure of cells to test compound was assayed by quantitating total P388 cells on a Coultier Counter following a 48-hour co-incubation of test compound with cells. P388 cells were maintained in log phase throughout the duration of cytotoxicity assays.

The percentage of cells surviving relative to an untreated control was graphed as a function of increasing drug concentration. The $IC_{50}$ is defined as that concentration of drug which reduced the population of viable cells to 50% that of an untreated control.

TABLE 4

IN VITRO CYTOTOXICITY OF REPRESENTATIVE EXAMPLES OF COMPOUND I

| Example | WIN | $IC_{50}$ (μM) P388 1 hr. exp. | $IC_{50}$ (μM) P388 cont. exp. |
|---|---|---|---|
| 1 | 64589 | 80 | 20 |
| 2 | 65127 | 1.6 | N.D. |
| 3 | 63223 | 7.3 | 7.1 |
| 4 | 63647 | N.D. | 4.0 |
| 5 | 64004 | N.D. | 18 |
| 6 | 64031 | 20 | 6.1 |
| 7 | 64123 | 21 | 14 |
| 8 | 64249 | 37 | 6.9 |
| 9 | 64250 | 20 | 6.1 |
| 10 | 64459 | N.D. | 8.5 |
| 11 | 64460 | N.D. | 8.9 |
| 12 | 64461 | >200 | 7.4 |
| 13 | 64540 | N.D. | 2.3 |
| 16 | 64877 | 0.93 | N.D. |
| 18 | 64894 | 1.1 | N.D. |
| 20 | 64985 | 0.25 | N.D. |
| 24 | 65074 | 0.39 | N.D. |
| 26 | 64593 | 0.25 | 0.055 |
| 27 | 64145 | 1.5 | 0.45 |
| 28 | 64146 | 8.2 | 4.6 |
| 29 | 64160 | 3.0 | 8.0 |
| 30 | 64266 | 0.67 | 0.29 |
| 31 | 64267 | 2.2 | 1.5 |
| 32 | 64462 | 0.60 | 1.4 |
| 33 | 64463 | 0.21 | 0.061 |
| 34 | 64476 | 0.88 | 0.32 |
| 35 | 64860 | 0.47 | N.D. |
| 37 | 64986 | 125 | N.D. |
| 38 | 65048 | 0.36 | N.D. |

N.D. = No Data

Representative examples of the compounds of formula I were also tested for antitumor activity in mice against several tumor systems, as described more fully below, and were found to possess antineoplastic activity as evidenced by their activity in reducing the size of and curing tumors, and increasing the survival time of the mice.

In Vivo Antitumor Assay Procedure

Mice: Inbred: C3H/He and NCR-nu; and Hybrids: B6D2F1 (C57BL/6 females X DBA/2 males, CD2F1 (Balb/c females X DBS/2 males) and B6x C3f1 (C57BL/6 x C3H) were bred at Wayne State University from strained obtained from the Frederick Cancer Research Facility, Frederick, Md. or purchased from commercial suppliers.

Tumors: Murine Tumor: P388 and an adriamycin-resistant (ADR) subline P388/ADR leukemia and the following transplantable solid tumors of mice were used for in Vivo testing: B16 melanoma (B16), pancreatic ductal adenocarcinoma No. 03 (Panc 03), colon adenocarcinoma No. 38 (colo 38), mammary ductal adenocarcinoma No. 16/C (Mam16) and an adriamycin-resistant subline Mam16C/ADR. Human tumor: A single human tumor, mammary carcinoma MX-1 (MX1) was used for in vivo testing. All tumors are in the Developmental Therapeutics Program frozen tumor respository, maintained by the Biological Testing Branch, Frederick Md. Each has a detailed description, code identification number, and list of references at the National Tumor Repository. Murine tumors were maintained in the mouse strain of origin and were transplanted in the appropriate F1 hydrid (or the strain of origin) for therapy trials. Human mammary carcinoma MX-1 MX1) was maintained as a subcutaneous implant in either athymic Swiss (Cr: NIH(S)-nu) or athymic random bred (NCR-nu) mice and transplanted in NCR-nu for therapy trials.

Chemotherapy: For pancreatic ductal adenocarcinoma No. 3, colon adenocarcinoma No. 38 (colo38), lung carcinoma No. 12 (LC12) and both adriamycin-sensitive (RP) and -resistant ADR) mammary ductal adenocarcinoma No. 16 (Mam16) tumors, the following methods were used to help ensure a more uniform tumor burden per mouse (thus reducing the requirement for greater numbers of mice per group), bilateral tumor implants were used. The animals necessary to begin an experiment were pooled, implanted bilaterally s.c. on day zero with 30–60-mg tumor fragments using a 12-gauge trocar, and again pooled before randomization to the various treatment and control groups. Chemotherapy was started within three days after tumor implantation while the number of cells per mouse was relatively small ($1 \times 10^7$—$a \times 10^8$ cells).

For P388 and P388/ADR leukemia studies the tumor cells were implanted either IP or intravenously (IV) on day zero and treatment was started on day one. For B16 melanoma (B16) studies, the tumor cells were implanted IP on day zero and treatment was started on day one. Tirered controls were also included to facilitate the calculation of tumor cell kill. For mammary carcinoma MX-1 studies, tumors were implanted with 1) subcutaneously (sc) (14-mg fragment of s.c. donor tumor) in the axillary region or 2) under the subrenal capsule (src) ($10 \times 10 \times 10$ ocular micrometer unit fragment of s.c. donor tumor). Treatment started on the day after subrenal capsule tumor implant or when the subcutaneous tumor implant had reached 100–700 mg.

End Points for Assessing Antitumor Activity:

Quantitative end points used assess antitumor activity included % Increased Life Span (% ILS), Tumor Cell Kill (Log10 kill), and Tumor Growth Inhibition (T/C). Long Term Survivors (45 or 60 day) were excluded from calculations of % ILS and Tumor Cell Kill.

Endpoints were calculated as follows: % ILS $$\% ILS = \frac{D_t - D_c}{D_c} (100)$$

where $D_t$ is the median day of death for treated and $D_c$ is the median day of death for control groups. A % ILS $\geq 20$ or $\geq 25$ for P388 and B16 intraperitoneal models, respectively, is indicative of a significant degree of antitumor activity. A % ILS $\geq 75$ or $\geq 50$ for P388 and B16 intraperitoneal models, respectively, is indicative of a high degree of antitumor activity and is the level used by National Cancer Institute to justify further development if other requirements are met (termed DN-2 level activity). Minimum quantitative activity limits for additional P388 models (e.g. P388/ADR and P388, IJV) have not been defined. However, the activity limits specified for the intraperitoneal models may be applied as in the majority of instances these models are found to be signficantly less challenging.

Tumor Cell Kill

The $\log_{10}$ cell kill was calculated from the following formula:

$$\text{Log}_{10} \text{ kill (total)} = \frac{T - C}{(3.32)(Td)}$$

where T-C is the tumor difference in the median day of death between the treated (T) and the control (C) groups and Td is the tumor doubling time (in days), the latter estimated from the best fit straight line from a log-linear growth plot of the control-group tumors in exponential growth. The conversion of the T-C values to $\log_{10}$ cell kill is possible because the Td for tumors regrowing post-treatment approximated the Td values of the tumors in untreated control mice.

T/C Value

Tumors were measured with a caliper once or twice weekly (as needed) until either tumors exceeded 1600 mg or cure was assured. Tumor weights were estimated from two-dimensional measurements: Tumor Weight (mg)=$(a \times b^2)$ / 2, where a and b are the tumor length and width (nun) respectively. Measurements were carried out simultaneously in both treatment and control groups. When the control group tumors reached approximately 750–1500 mg in size (median of group), the median tumor weight of each group was determined (including zeros). The T/C value in percent is an indiation of antitumor effectiveness. The % T/C was calculated from the following formula for solid murine tumor models:

$$\% T/C = \frac{T}{C} \times 100$$

where T and C are median tumor weights of the treatment and control groups, respectively. A T/C equal to or less than 42% is considered significant antitumor activity. A T/C value <10% is indicative of a high degree of antitumor activity and is the level used by National Cancer Institute to justify further development if other requirements are met (termed DN-2 level activity). By convention the T/C value for the mammary carcinoma MX-1 models is calculated by the parameter of change in tumor weight. The % T/C was calculated from the following formula for MX-1 models $$\% T/C = \frac{\Delta T}{C} \times 100 \text{ (if } \Delta T \text{ is positive)}$$

$$\% T/C = \frac{\Delta T}{T \text{(initial)}} \times 100 \text{ (if } \Delta T \text{ is negative)}$$

where $\Delta T$ and $\Delta C$ are the change in mean tumor weight of the test and control groups, respectively, and T (initial) is the initial mean tumor weight of the test group. An initial %T/C $\leq 20$ is considered necessary to demonstrate moderate activity. A reproducible % T/C ≦ 10 is considered significant activity.

Activity

All in vivo trials are summarized in Table 5.

TABLE 5

| | | In vivo activity of compounds of formula I | | | | | |
|---|---|---|---|---|---|---|---|
| EXAMPLE | MODEL | DRUG ROUTE | SCHEDULE | MTD MG/KG | T/C % | ILS % | LOG KILL |
| 3 | Panc03(sc) | sc | qd 3–12 | 3749[1] | >100 | | |
| 18 | Panc03(sc) | iv, sc | iv; qd 3 bid 4–9 sc; bid 10–11 | 88 | 21[1] | | |
| 20 | Panc03(sc) | iv, sc | iv; qd 3,5 bid 4,6–8 sc; bid 9–11 qd 12 | 336 | 80 | | |
| 26 | B16(ip) | ip | qd 1,5,9 | 8.1 | | 94 | 2.2 |
| | Colo38(sc) | iv | qd 3–5 bid 6–11 | 30 | 46 | | |
| | Mam16C(sc) | iv | qd 1, bid 2,3 | 15 | 28 | | 0.90 |
| | Mam16C/ADR | iv | qd 1 bid 2,3 | 30 | 71 | | |
| | MX1(src) | ip | qd 1,5,9 | 8.1 | 20 | | |
| | P388(ip) | ip | qd 1,5,9 | 12 | | 100 | 7.3 |
| | P388(ip) | iv | qd 1,5,9 | 15 | | 80 | 5.8 |
| | Panc03(sc) | sc | qd 3,5–7 bid 4 | 840 | 19[3] | | |
| | Panc03(sc) | iv | qd 4–11 | 12 | 0[3] | | 1.7 |
| 30 | B16(ip) | ip | qd 1,5,9 | 304 | | 88 | 2.0 |
| | Colo38(sc) | iv | qd 3–11 | 148 | 42 | | |
| | MX1(src) | ip | qd 1,5,9 | 304 | 6 | | |
| | P388(ip) | ip | qd 1,5,9 | 456 | | 120 | 8.8 |
| | P388(ip) | iv | qd 1,5,9 | 120 | | 20 | 1.5 |
| | Panc03(sc) | iv | qd 3–11 | 235 | 5 | | |
| 33 | B16(ip) | ip | qd 1,5,9 | 19 | | 94 | 2.2 |
| | Colo38(sc) | iv | qd 3–11 | 33 | >100 | | |
| | MX1(src) | ip | qd 1,5,9 | 19 | 8 | | |
| | P388(ip) | ip | qd 1,5,9 | 19 | | 50 | 3.6 |
| | P388(ip) | iv | qd 1,5,9 | 37 | | 50 | 3.6 |
| | Panc03(sc) | iv | qd 3–4,7,10 | 19 | 73 | | |

[1]MTD not achieved-maximum dose tested.
[2]2 lower doses equally active to modestly more active.
[3]1/6 tumor free long term survivor.

In practicing the method of the invention, the therapeutic dose of the compound of formula I to be administered to the mammal afflicted with malignant cells is that amount which is effective to inhibit mammalian topoisomerase II and thereby to inhibit the growth of, kill or induce the regression of the malignant cells, or to prolong the life of the mammal.

The specific amount of formula I constituting a therapeutically effective dose and the length of treatment required will vary since it is dependent on a number of factors such as, for example, the size, age, condition and species of the mammal to be treated, the degree of involvement of the malignancy, the specific compound to be administered and its bioavailability, the dose regimen and the mode of administration. The specific amount to be employed for a particular afflicted mammal is readily determinable by the skilled artisan using conventional techniques.

In practicing the invention, the compounds can be administered to the mammal orally or parenterally.

The compounds can be prepared for use by incorporation them in conventional, pharmaceutically acceptable diluents, carriers or excipients. For parenteral administration (intravenous, intraperitoneal, subcutaneous or intramuscular), the compounds are dissolved or suspended in an aqueous or nonaqueous vehicle. For oral administration, the compounds are formulated in dosage unit form as tablets or capsules. Exemplary diluents, carriers or excipients include lactose, dextrose, sucrose, sorbitol, mannitol, starches, gum acacia, calcium phosphate, mineral oil, cocoa butter, alginates, tragacanth, gelatin, methyl cellulose, methyl- and propyl hydroxybenzoates, talc, magnesium stearate and the like.

We claim:

1. A compound of formula

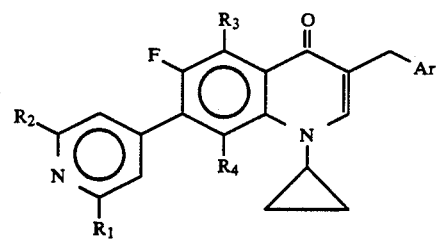

wherein
- $R_1$ is hydrogen, lower-alkyl, or trifluoromethyl;
- $R_2$ is lower-alkyl, trifluoromethyl or $CH_2Z$ where Z is hydroxy, chloro, lower-alkylamino or dilower-alkylamino;
- $R_3$ and $R_4$ are each independently hydrogen or fluoro; and
- Ar is phenyl, an aromatic 5- or 6-membered heterocycle having carbon and up to two heteroatoms chosen from nitrogen and oxygen; or any of these substituted at one to three positions with lower-alkyl, fluoro, chloro, hydroxy, amino, lower-alkylamino, dilower-alkylamino, carboxy, sulfonamido, lower aklylsulfonamido, methylenedioxy, trifluoroacetamido, lower-alkanoylamino, or carbanoyl;

or a pharmaceutically acceptable acid addition salt thereof.

2. A compound according to claim 1 wherein $R_1$ and $R_2$ are methyl, $R_3$ is hydrogen, and $R_4$ is fluoro.

3. A compound according to claim 2 wherein Ar is chosen from the group consisting of phenyl, pyridyl or imidazolyl or substituted phenyl, pyridyl or imidazolyl.

4. A compound according to claim 3 wherein Ar is phenyl substituted with one or more of methyl, hydroxy, carboxy, $NHSO_2CH_3$, $NHCOCF_3$, $NHCOCH_3$, fluoro, chloro, or 3,4-methylenedioxy.

5. A compound according to claim 4 wherein Ar is phenyl 2-imidazolyl, 2-hydroxyphenyl, 2,4-dihydroxyphenyl or 2,6-dihydroxyphenyl.

6. A compound of formula

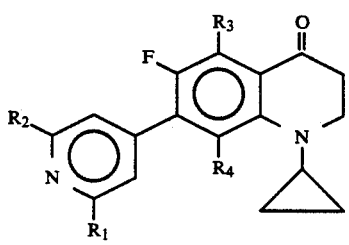

wherein $R_1$ is hydrogen, lower-alkyl, or trifluoromethyl;

$R_2$ is lower-alkyl, trifluoromethyl or $CH_2Z$ where Z is hydroxy, chloro, lower-alkylamino or dilower-alkylamino and $R_3$ and $R_4$ are each independently hydrogen or fluoro.

7. A compound according to claim 6 wherein $R_1$ and $R_2$ are methyl, $R_3$ is hydrogen, and $R_4$ is fluoro.

8. A compound of formula

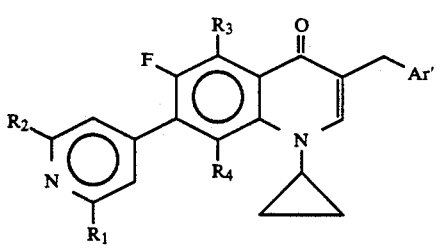

wherein $R_1$ is hydrogen, lower-alkyl, or trifluoromethyl;

$R_2$ is lower-alkyl, trifluoromethyl or $CH_2Z$ where Z is hydroxy, chloro, lower-alkylamino of dilower-alkylamino $R_3$ and $R_4$ are each independently hydrogen or fluoro; and Ar' is phenyl substituted with one or more of lower-alkoxy or benzyloxy wherein Ar' also includes 3,5-$(CH_3O)_2$-4-OH-phenyl.

9. A compound according to claim 8 wherein Ar' is phenyl substituted with one lower alkoxy group.

10. A compound according to claim 8 wherein Ar' is 2,5-$(CH_3O)_2$-phenyl, 2,6-$(CH_3O)_2$-phenyl, 3,5-$(CH_3O)_2$-4-OH-phenyl.

11. A pharmaceutical composition comprising a pharmaceutical carrier and a compound according to claim 1 in a sufficient amount to treat the growth of malignant cells susceptible to the action of such compound.

12. A pharmaceutical composition comprising a pharmaceutical carrier and a compound according to claim 2 in a sufficient amount to treat the growth of malignant cells susceptible to the action of such compound.

13. A pharmaceutical composition comprising a pharmaceutical carrier and a compound according to claim 3 in a sufficient amount to treat the growth of malignant cells susceptible to the action of such compound.

14. A pharmaceutical composition comprising a pharmaceutical carrier and a compound according to claim 4 in a sufficient amount to treat the growth of malignant cells susceptible to the action of such compound.

15. A pharmaceutical composition comprising a pharmaceutical carrier and a compound according to claim 5 in a sufficient amount to treat the growth of malignant cells susceptible to the action of such compound.

16. A pharmaceutical composition comprising a pharmaceutical carrier and a compound according to claim 9 in a sufficient amount to treat the growth of malignant cells susceptible to the action of such compound.

17. A pharmaceutical composition comprising a pharmaceutical carrier and a compound according to claim 10 in a sufficient amount to treat the growth of malignant cells susceptible to the action of such compound.

18. A method of treating malignant cell growth in a host, such cells being susceptible to the action of a compound according to claim 1, which comprises administering to said host an effective amount of such compound.

19. A method of treating malignant cell growth in a host, such cells being susceptible to the action of a compound according to claim 2, which comprises administering to said host an effective amount of such compound.

20. A method of treating malignant cell growth in a host, such cells being susceptible to the action of a compound according to claim 3, which comprises administering to said host an effective amount of such compound.

21. A method of treating malignant cell growth in a host, such cells being susceptible to the action of a compound according to claim 4, which comprises administering to said host an effective amount of such compound.

22. A method of treating malignant cell growth in a host, such cells being susceptible to the action of a compound according to claim 5, which comprises administering to said host an effective amount of such compound.

23. A method of treating malignant cell growth in a host, such cells being susceptible to the action of a compound according to claim 9, which comprises administering to said host an effective amount of such compound.

24. A method of treating malignant cell growth in a host, such cells being susceptible to the action of a compound according to claim 10, which comprises administering to said host an effective amount of such compound.

* * * * *